United States Patent
Appelbaum et al.

[11] Patent Number: 6,010,496
[45] Date of Patent: Jan. 4, 2000

[54] VITRECTOMY TIMING DEVICE WITH MICROCONTROLLER WITH PROGRAMMABLE TIMERS

[75] Inventors: Peter Francis Appelbaum, Ballwin; John Alan Ritter, Des Peres, both of Mo.

[73] Assignee: Bausch & Lomb Surgical, Inc., Claremont, Calif.

[21] Appl. No.: 08/918,711

[22] Filed: Aug. 22, 1997

Related U.S. Application Data

[60] Provisional application No. 60/025,498, Aug. 29, 1996, abandoned.

[51] Int. Cl.⁷ .............................. A61B 17/00; G06F 15/00
[52] U.S. Cl. ......................... 606/4; 606/166; 364/413.01
[58] Field of Search ....................... 604/22, 65; 606/166, 606/170, 171, 18, 168, 4; 364/413.01, 413.02; 137/870, 883

[56] References Cited

U.S. PATENT DOCUMENTS

| | | |
|---|---|---|
| 4,024,866 | 5/1977 | Wallach . |
| 4,117,843 | 10/1978 | Banko . |
| 4,168,707 | 9/1979 | Douvas et al. . |
| 4,180,074 | 12/1979 | Murry et al. . |
| 4,314,560 | 2/1982 | Helfgott et al. . |
| 4,428,748 | 1/1984 | Peyman et al. . |
| 4,525,775 | 6/1985 | Eydelman . |
| 4,622,503 | 11/1986 | Sunblom et al. . |
| 5,033,496 | 7/1991 | Reid . |
| 5,094,260 | 3/1992 | Stuart et al. . |
| 5,157,603 | 10/1992 | Scheller et al. . |
| 5,158,108 | 10/1992 | Semaan et al. . |
| 5,176,628 | 1/1993 | Charles et al. . |
| 5,417,246 | 5/1995 | Perkins et al. . |
| 5,455,766 | 10/1995 | Scheller et al. . |
| 5,549,139 | 8/1996 | Perkins et al. . |

*Primary Examiner*—Michael Buiz
*Assistant Examiner*—William W. Lewis
*Attorney, Agent, or Firm*—Senniger, Powers, Leavitt & Roedell

[57] ABSTRACT

A system for controlling a plurality of ophthalmic microsurgical instruments connected thereto. The microsurgical instruments are for use by a user such as a surgeon in performing ophthalmic surgical procedures. The system includes a data communications bus and a user interface connected to the data communications bus. The user interface provides information to the user and receives information from the user which is representative of operating parameters of the microsurgical instruments. The system also includes surgical modules connected to and controlling the microsurgical instruments as a function of at least one of the operating parameters. The surgical modules are also connected to the data communications bus. The data communications bus provides communication of data representative of the operating parameters between the user interface and the surgical modules. Other features are also disclosed including a main control, an endo-illuminator system, a phacoemulsification handpiece, surgical scissors, a vitrectomy cutter, a surgical foot control, a remote control, a cart.

11 Claims, 13 Drawing Sheets

VITRECTOMY TIMING DEVICE WITH MICROCONTROLLER WITH PROGRAMMABLE TIMERS

This application claims benefit of Provisional Application No. 60/025,498 filed Aug. 29, 1996.

BACKGROUND OF THE INVENTION

This invention relates generally to vitrectomy control systems for vitrectomy probes.

The eye is divided into two sections, the anterior section and the posterior section. The anterior section contains the cornea, iris, anterior chamber, ciliary body and lens. The posterior section contains the vitreous, retina, choroid and sclera. Certain ophthalmic surgical procedures require the incision and removal of all or part of the vitreous in the eye. This procedure is known as vitrectomy and surgical instruments commonly known as vitrectomy probes have been developed for this purpose.

Vitrectomy probes typically comprise a stationary outer needle which contains one or more apertures to receive the vitreous when suction is applied. A cutting blade located within the outer needle cuts the fibers of the vitreous as it is drawn into the needle. The cutting blade of the vitrectomy probe is typically driven via pneumatic or electrical pulses generated from a pneumatic or electrical source, respectively. The interval between pulses (i.e., period) defines the cut rate of the cutting blade of the vitrectomy probe. The duration of each pulse and the pulse period in turn define the drive characteristics of the vitrectomy probe.

Different surgical techniques require different drive characteristics. Accordingly, a variety of different types of vitrectomy probes having different drive characteristics have been developed. The structure of the various areas of the posterior section of the eye are also significantly different. Some areas, such as the retina, are more sensitive than other areas. Moreover, the structure of the eye itself is different from individual to individual. Therefore, a specific concern in the use of vitrectomy probes is the ability to accurately, reliably and automatically control its drive characteristics on demand in order to accommodate all of these various differences.

Existing vitrectomy control systems use pneumatic delay valves, monostable multivibrators, external microprocessor peripheral timing chips or external programmable, logic-based counters to control the drive characteristics of vitrectomy probes. However, because of limitations in complexity due to both cost and hardware constraints, the parameters for the pulse duration which in part defines the drive characteristics of the vitrectomy probe are set by loading pre-selected timing values into the external peripheral chips, discrete counters or programmable logic. Any changes in these pulse duration parameters require a significant hardware redesign. Moreover, these changes typically cannot be implemented by a surgeon or nurse, but rather require a trained technician. The above-mentioned hardware constraints of existing vitrectomy control systems therefore severely limit the types and number of vitrectomy probes that can be supported by any given system.

The above-mentioned limitations not only affect the functional or performance aspects of a vitrectomy probe, but also have a significant affect on its reliability and safety. The timing mechanisms implemented by existing vitrectomy control systems require several integrated circuits and interconnections. Each additional circuit and each additional interconnection, however, increases the risk of failures and defects and thus, decreases the reliability and safety of the probe. In some cases, such failures and defects can cause serious injury to the eye. The complexity of the hardware also increases the overall cost of the vitrectomy control system.

Accordingly, a need has arisen for a vitrectomy control system for accurately, reliably and automatically controlling the drive characteristics of a vitrectomy probe on demand by a user over a wide range of pulse durations and cut rates.

SUMMARY OF THE INVENTION

One aspect of the invention relates to a control system for surgical instruments which comprises a surgical instrument having a pulse-driven member and a pulse generator adapted to generate a plurality of pulses for driving the pulse-driven member, the plurality of pulses defining a pulse interval between each of the pulses, and each of the plurality of pulses having a pulse duration, the pulse interval and the pulse duration defining a pulse-driven member rate for the pulse-driven member of the surgical instrument. The pulse-driven member may comprise a vitrectomy probe having a cutting blade and the plurality of pulses generated by the pulse generator may be either pneumatically or electrically driven.

The system further includes a control mechanism coupled to the pulse generator for controlling the pulse duration and the pulse-driven member rate such that the pulse duration and pulse-driven member rate can be automatically changed over a wide range of pulse durations and pulse-driven member rates, respectively, on demand by an operator of the control system. The control mechanism preferably comprises a microcontroller having built-in software controlled logic adapted to control the pulse duration and the pulse interval of the pulse generated by the pulse generator. In one preferred embodiment of the invention, the software controlled logic of the microcontroller comprises a first timer for controlling the pulse duration of the pulse generated by the pulse generator, and a second timer for controlling the pulse interval of the plurality of the pulses generated by the pulse generator. In another preferred embodiment of the invention, the software-controlled logic of the microcontroller comprises a timer adapted to control the pulse duration of each of the pulses generated by the pulse generator, and at least one clock interrupt adapted to control the pulse interval. The pulse-driven member rate preferably ranges between 30 cuts/minute and 990 cuts/minute and comprises a rate changing mechanism for changing the pulse-driven member rate in increments of 30 cuts/minute.

Another aspect of the invention relates to a microsurgical system which comprises a console and a plurality of ophthalmic modules removably coupled within the console of the microsurgical system. One of the ophthalmic modules comprises a surgical instrument port adapted to receive a surgical instrument and a control system for controlling the surgical instrument as previously described above.

DETAILED DESCRIPTION OF THE PREFERRED EMBODIMENTS

While the invention has been and will be described in detail with respect to the modular, ophthalmic microsurgical control system 1 of FIG. 1 and with respect to vitrectomy probes, it can be understood by one skilled in the art that the invention can be implemented in any microsurgical system or stand alone microsurgical device (as shown in FIG. 6), and in connection with any surgical instrument which is pulse-driven, either pneumatically or electrically.

Figure 1:
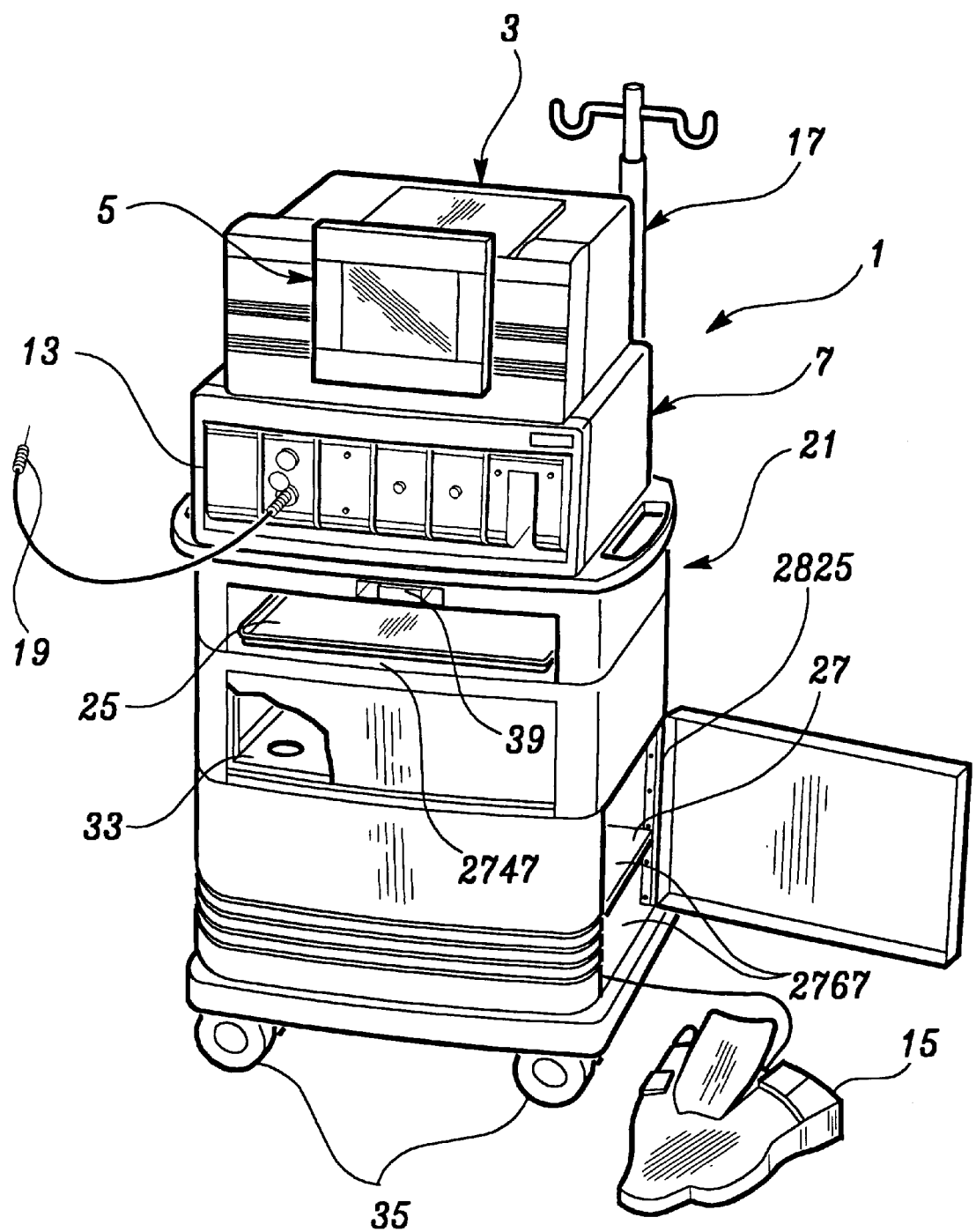
FIG. 1 is a perspective view of a microsurgical system.
Figure 2:
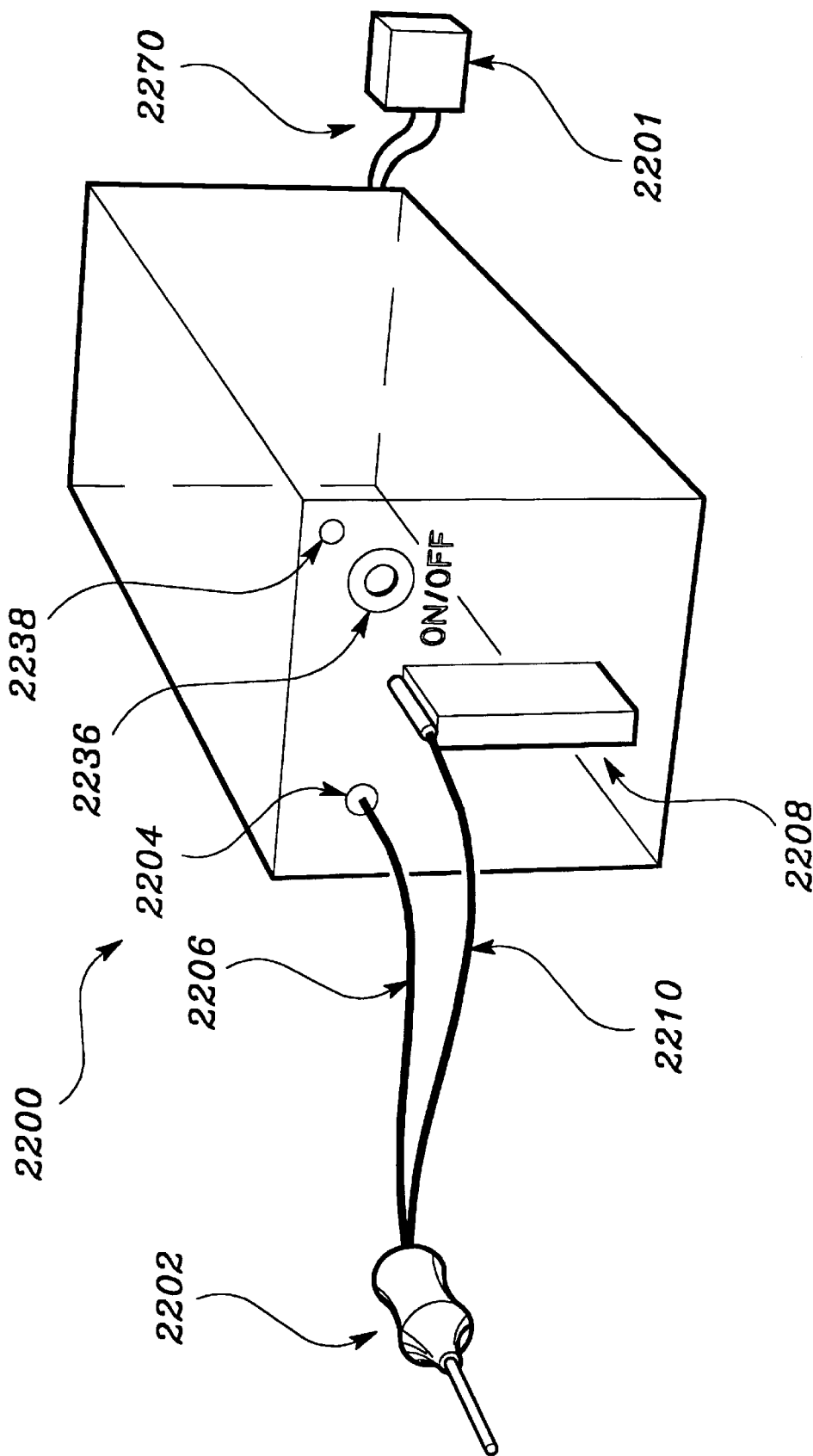
FIG. 2 is a perspective view of a vitrectomy module for use in a microsurgical system of FIG. 1.

Referring now to FIG. 2, there is generally shown a vitrectomy module 2200 and a vitrectomy probe 2202 (i.e., one of microsurgical instruments 19) connected thereto for use in microsurgical control system 1 of FIG. 1. Vitrectomy module 2200 houses a vitrectomy control system 2250 (see FIG. 5) for controlling the operation of vitrectomy probe 2202 as will be later described in more detail below. Once vitrectomy module 2200 is inserted into base unit 7 of microsurgical control system 1, the user can dynamically configure vitrectomy probe 2202 either through panel display 5 or foot control assembly 15 of microsurgical control system 1, or remotely through a serial communication port on computer unit 3 of microsurgical control system 1 (not shown) or through any other known manner of remote communication.

Vitrectomy probe 2202 is coupled to a vitrectomy port 2204 located on the front face of vitrectomy module 2200 through an inlet tube 2206. Vitrectomy probe 2202 is also coupled to a collection container or cassette 2208 retractably positioned within vitrectomy module 2200 via an aspiration tube 2210 through which vitreous fibers cut by vitrectomy probe 2202 may be transported. A pneumatic source 2201 is connected via a tube 2270 to vitrectomy module 2200 for providing a plurality of pneumatic pulses through inlet tube 2206 for driving vitrectomy probe 2202. Pneumatic source 2201 may be contained within the wall of the operating room or may be in the form of an external gas tank. Depending on the amount of air needed, pneumatic source 2201 may also be contained within vitrectomy module 2200 itself. Pneumatic source 2201 supplies pneumatic pulses to vitrectomy probe 2202 under pressure preferably ranging between 30 p.s.i. and 45 p.s.i.

Figure 3:
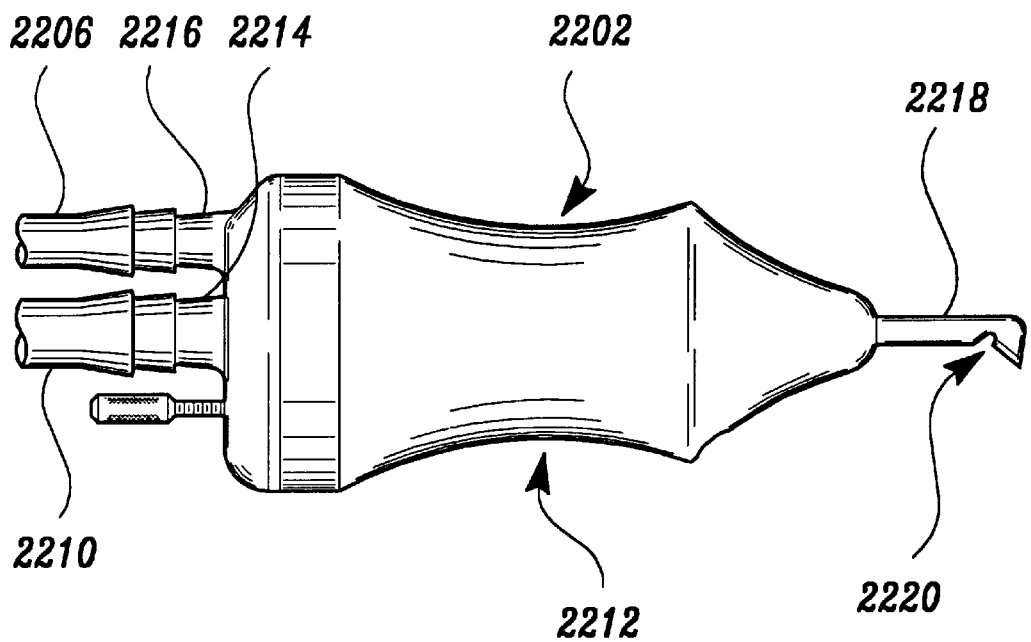
FIG. 3 is a side elevation of the vitrectomy probe of FIG. 2.
Figure 4:
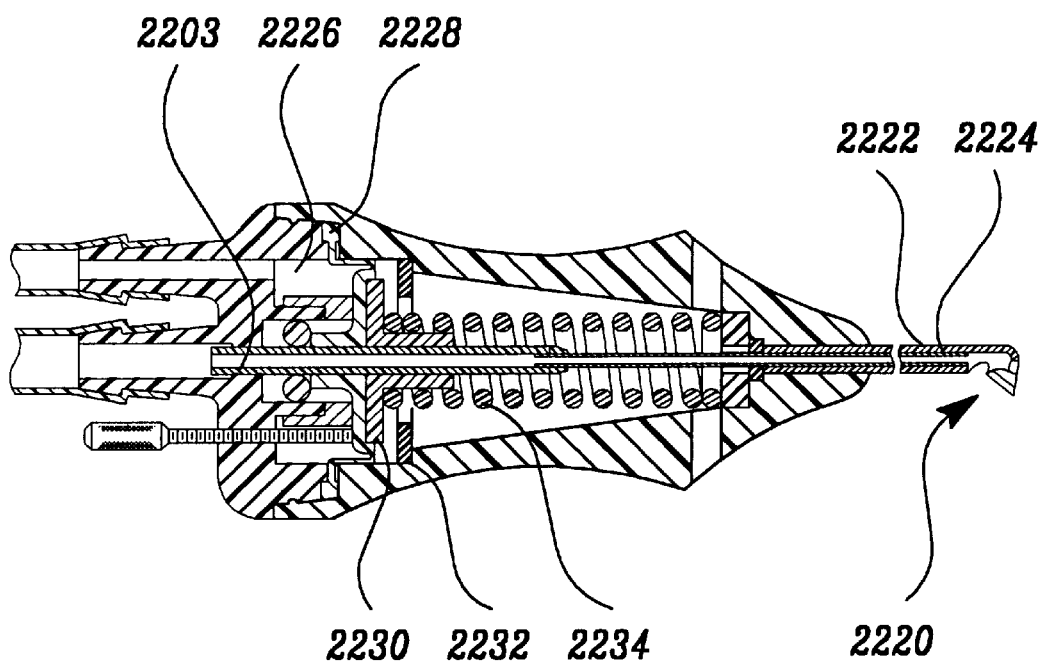
FIG. 4 is a cross-section of the vitrectomy probe of FIG. 3.
Figure 5A:
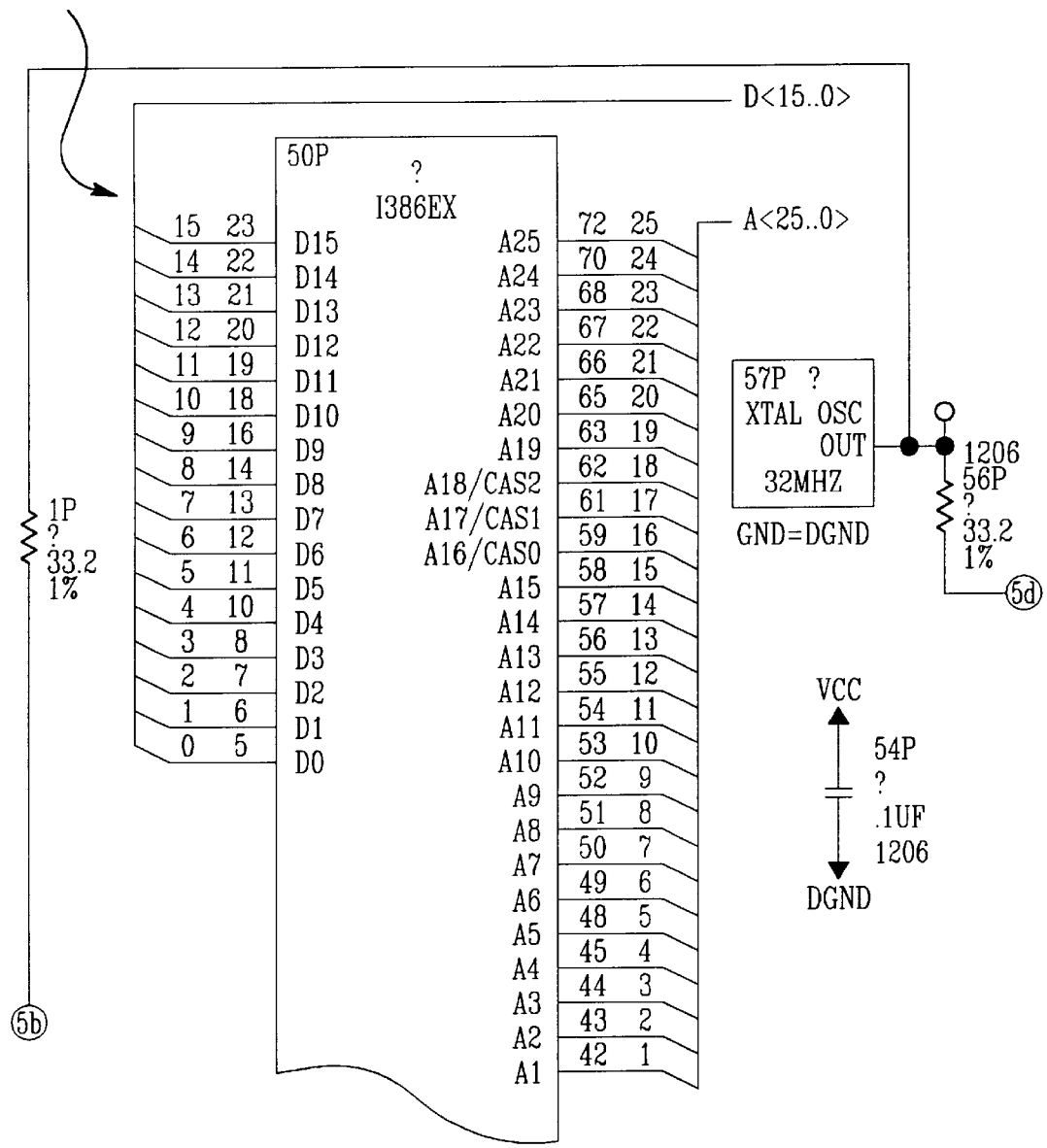
FIG. 5 is a detailed schematic drawing illustrating the circuitry of one embodiment of the vitrectomy control system in accordance with the present invention for use in the vitrectomy module of FIG. 2.
Figure 5B:
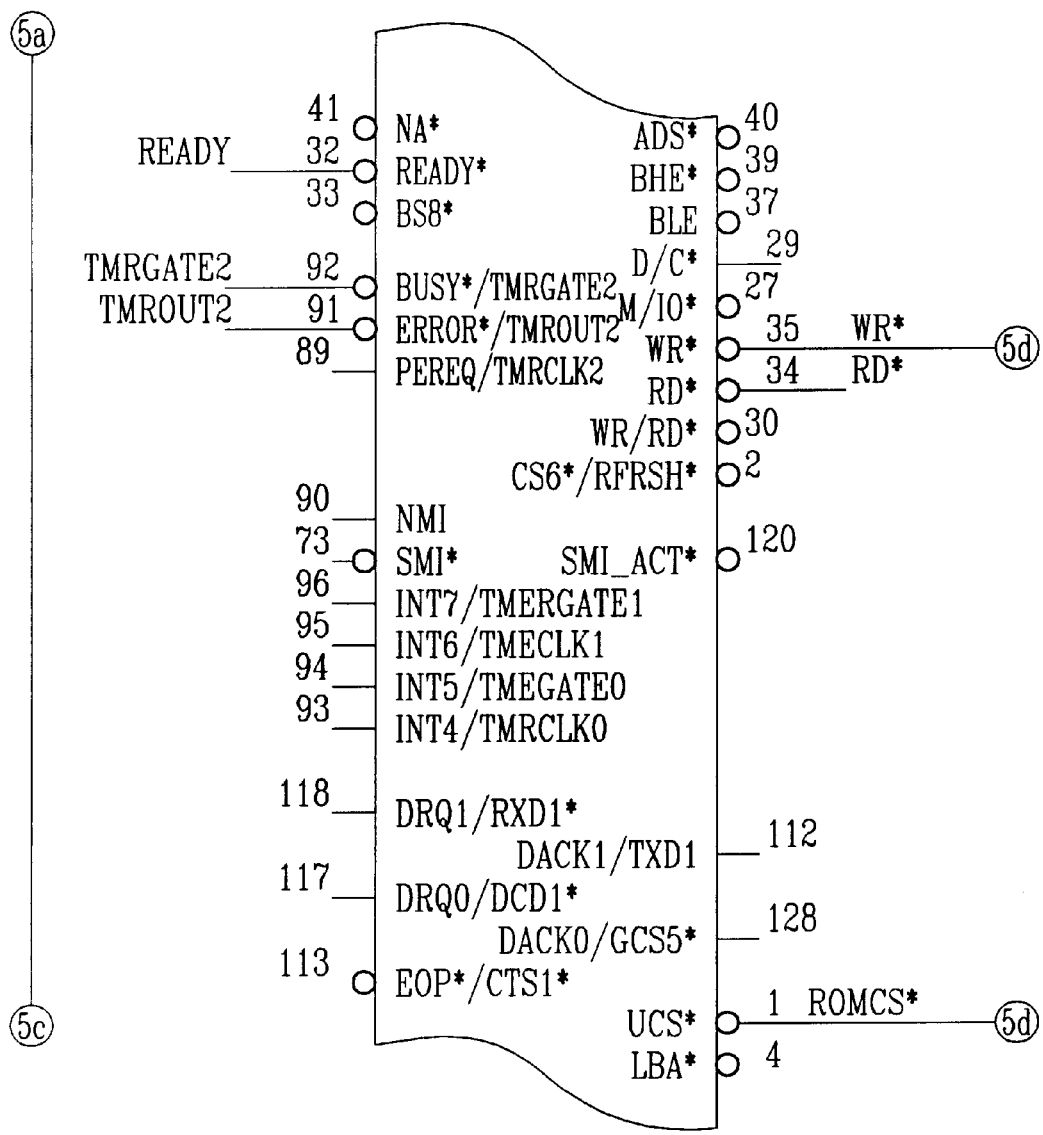
Figure 5C:
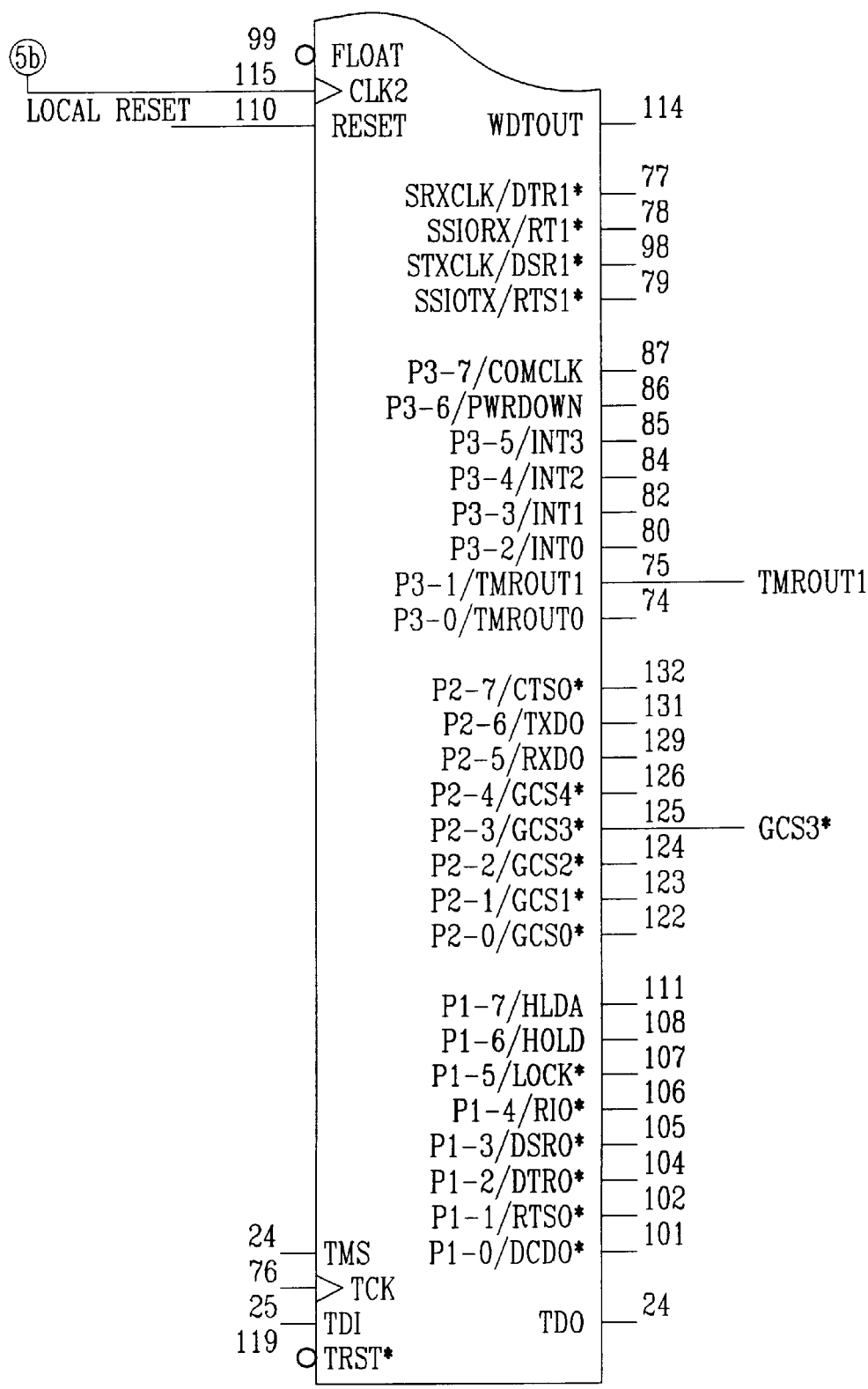
Figure 5D:
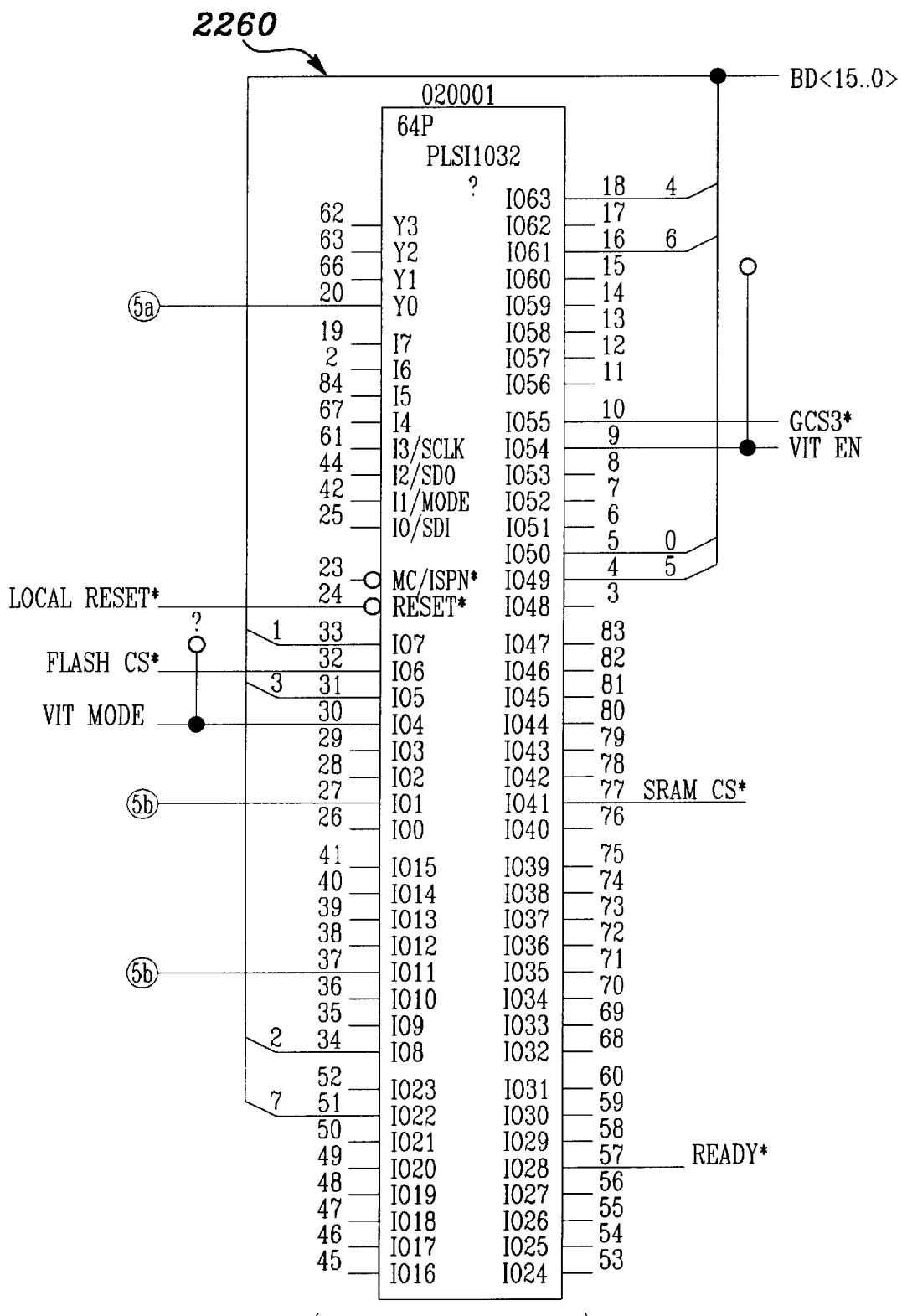
Figure 5E:
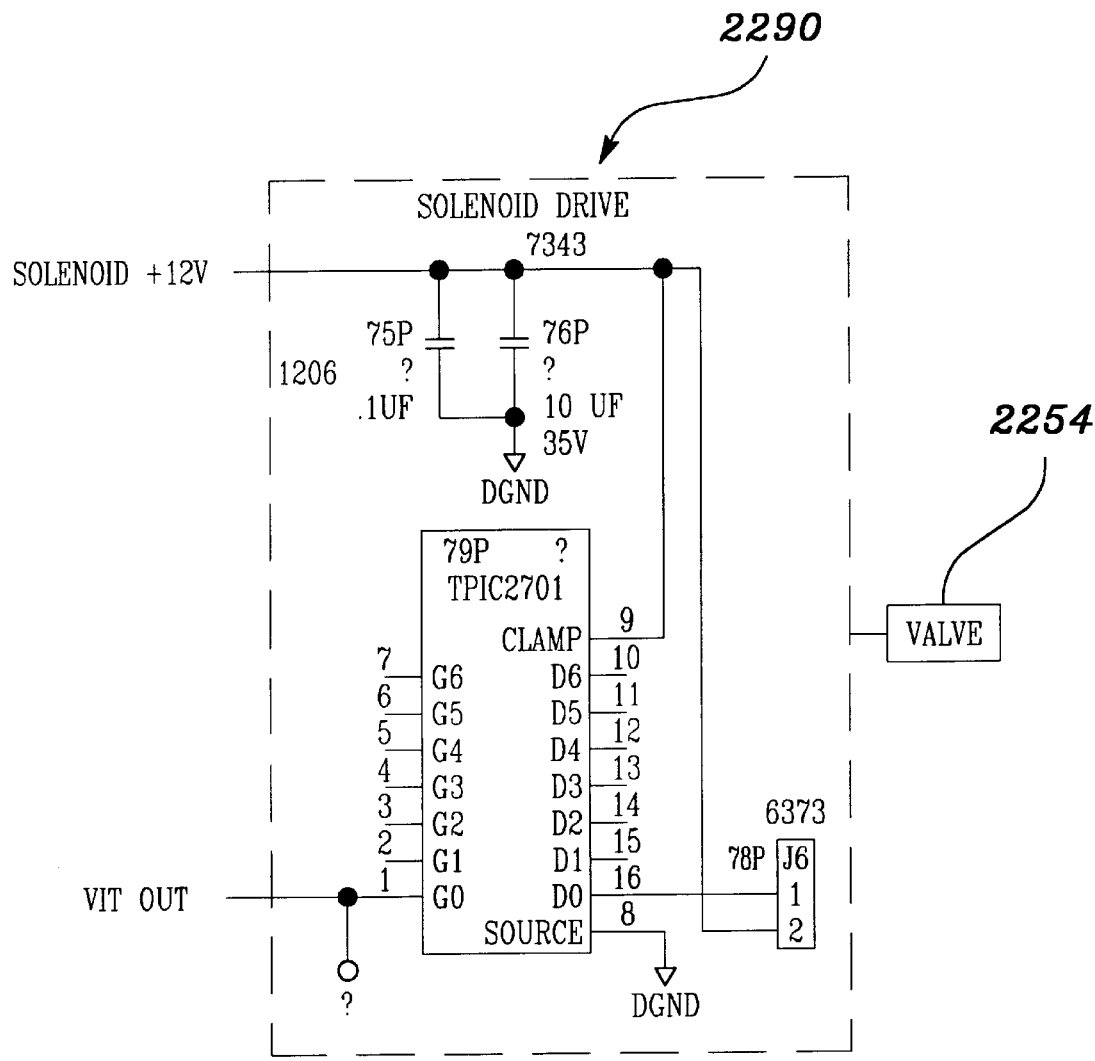
Figure 6A:
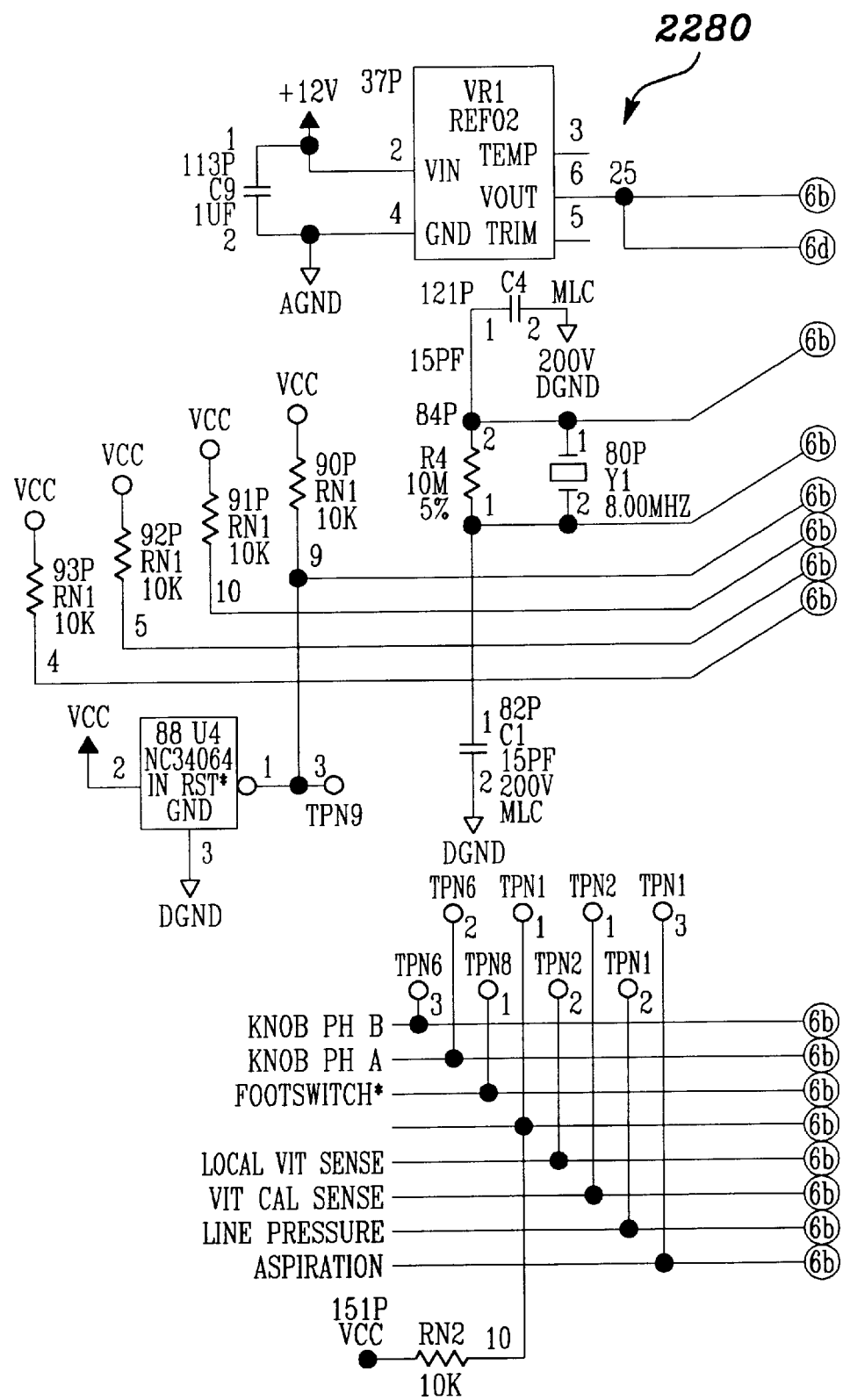
FIG. 6 is a detailed schematic drawing illustrating the circuitry of another embodiment of the vitrectomy control system in accordance with the present invention for use in a stand alone vitrectomy device.
Figure 6B:
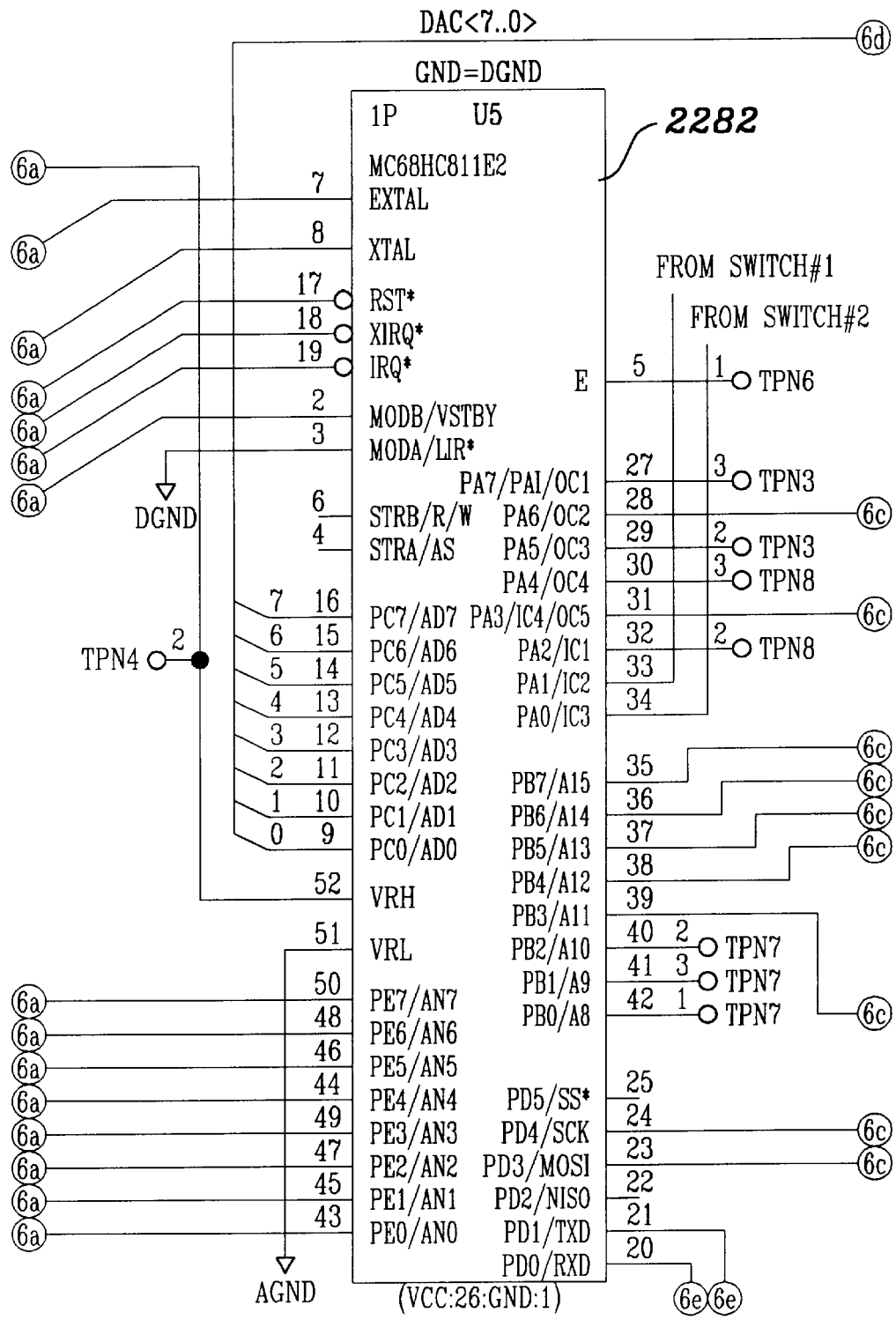
Figure 6C:
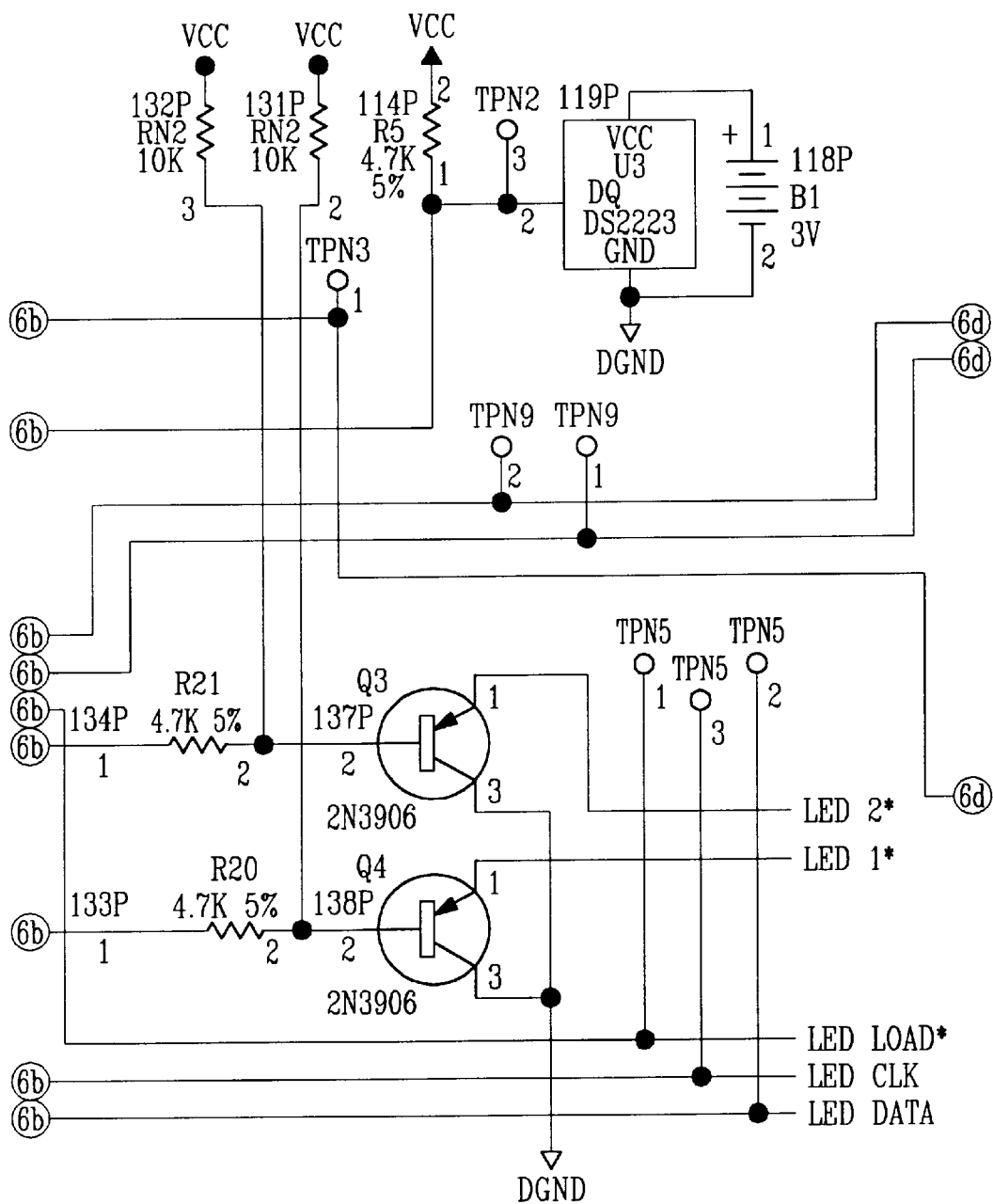
Figure 6D:
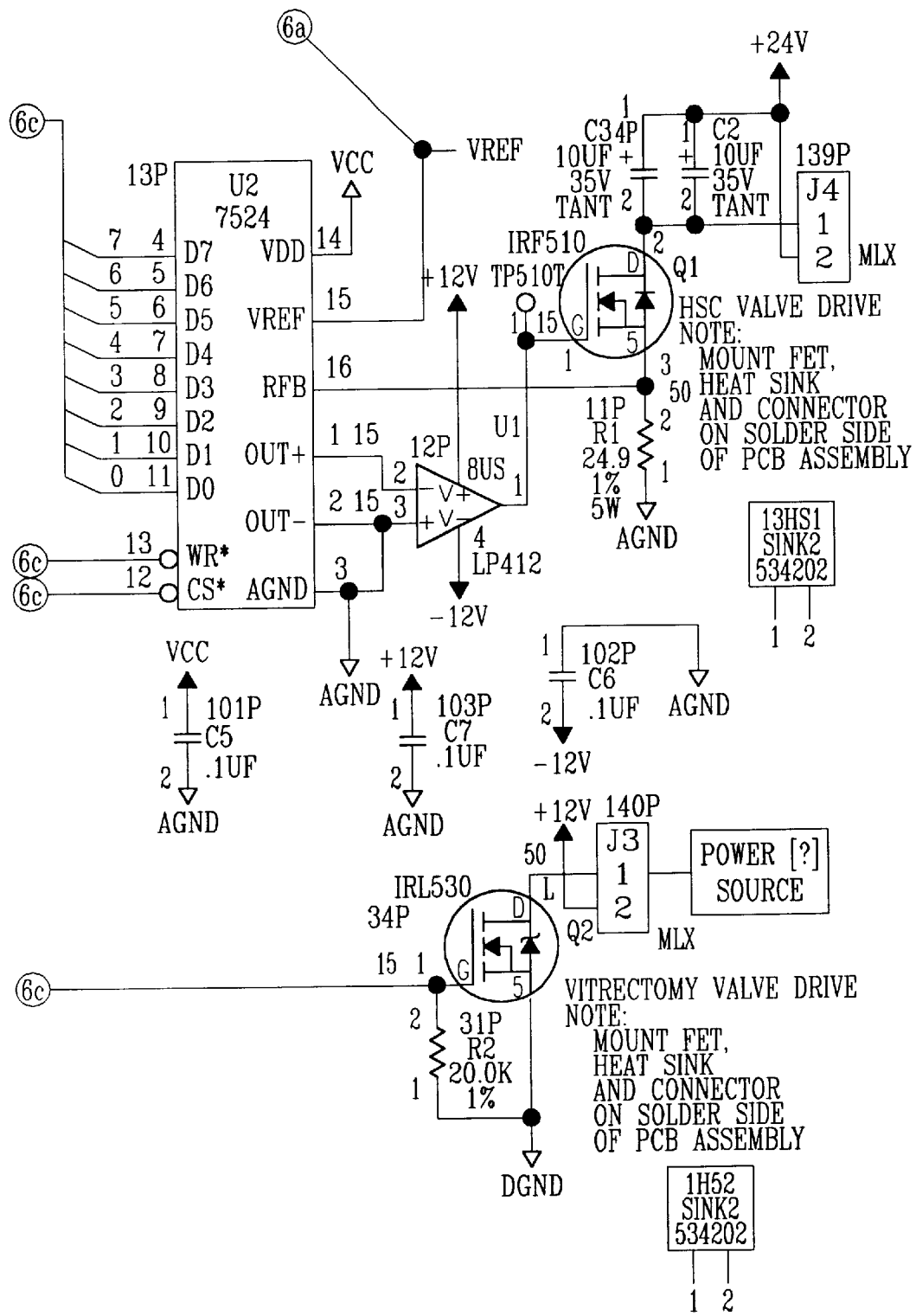
Figure 6E:
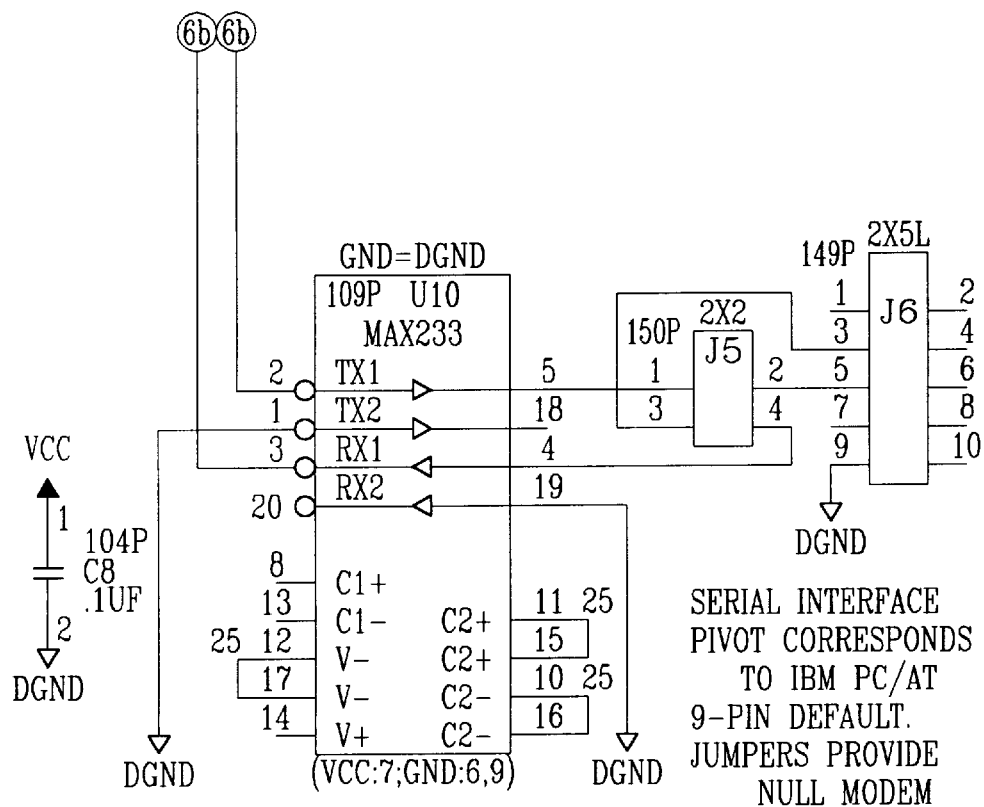
Figure 6E:
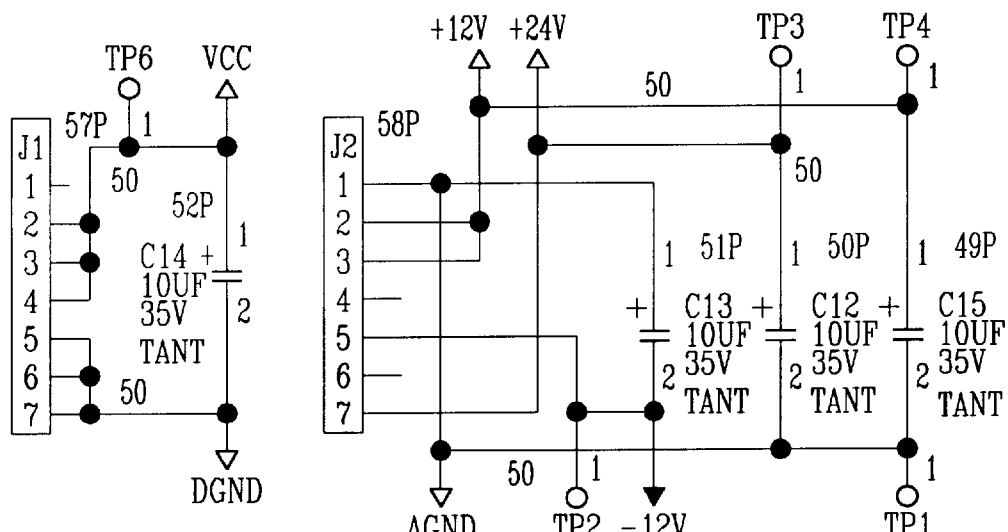

Referring now to FIG. 3, vitrectomy probe 2202 generally comprises a housing 2212 from which extends an aspiration fitting 2214 for receiving aspiration tube 2210, an inlet fitting 2216 for receiving inlet tube 2206, and a probe needle 2218 containing a vitreous inlet aperture or port 2200. Referring further to FIG. 4, inserted within probe needle 2218 is a hollow inner tubular member 2222 which extends into housing 2212 where it is attached to the end of a suction outlet tube 2203. A cutting blade 2224 is located on the outer end of inner tubular member 2222.

Cutting blade 2224 is reciprocably moved between a first position in which inlet port 2220 is open (i.e., the open position) and a second position in which inlet port 2220 is closed (i.e., the cutting position) by the application through inlet tube 2206 of pneumatic pulses generated by pneumatic source 2201. In particular, each pulse generated by pneumatic source 2201 is transported through inlet tube 2206 into a chamber 2226, which causes a diaphragm 2228 to push against a retainer 2230 which is connected to suction outlet tube 2203. Retainer 2230 and suction outlet tube 2203 are urged away from chamber 2226 toward a stop ring 2232, causing a spring mechanism 2234 to be compressed and inner tubular member 2222 and cutting blade 2224 to slide toward the cutting position. After each pulse is applied, spring mechanism 2234 forces retainer 2230, suction outlet tube 2210 and hence cutting blade 2224 back to the open position. While cutting blade 2224 is shown in FIG. 4 as a reciprocating blade which is pneumatically driven, it can be understood by one skilled in the art that the invention applies equally well to rotating-type cutting blades or surgical instruments that are driven by other types of signals, such as electrical signals.

Control of cutting blade 2224 of vitrectomy probe 2202 is performed via vitrectomy control system 2250 as shown in FIG. 5. Vitrectomy control system 2250 centers around a single chip microcontroller 2252. In a preferred embodiment, microcontroller 2252 is an Intel i386EX microcontroller operating at 16 MHz (e.g., coprocessor 469 in FIGS. 16 and 25E). The memory and I/O address map for microcontroller 2252 is specified in the Intel specification sheets for the i386EX microcontroller, which are incorporated herein by reference.

Microcontroller 2252 is coupled to a logic device 2260, such as a Lattice PLSI1032 erasable programmable integrated device, having counter and timer logic which is capable of controlling the duration and intervals of the pulses generated by pneumatic source 2201 through software. Use of such internal (i.e., built-in) hardware in vitrectomy control system 2250 eliminates the need for the external counters, peripheral chips and programmable logic of earlier vitrectomy control systems. Moreover, since the pulse duration is software controlled, vitrectomy module 2200 has the capability to accommodate a wide range of different types of vitrectomy probes which existing systems cannot.

Specifically, the clock of microcontroller 2252 provides the time base for two counters. One counter determines the pulse duration ("the pulse duration counter") and the other counter determines the pulse interval ("the pulse interval counter"). The pulse interval counter is preferably a 16 bit down counter with an input register. The inputs of the pulse duration counter include two chip select inputs from the address decode block, one for the lower input register and one for the higher input register. The inputs also include an enable bit from the control register block which can inhibit counting if necessary, a system reset, and an additional chip select which can cause the input latch values to be loaded into the timer register.

The outputs of the pulse duration counter include the outputs of the 16 bit input register for read back, a main ripple-count out ("RCO") output which is fed to the pulse width counter and causes the input register values to be loaded into the timer register, a main-eqv-0 output which indicates whether the input register contains all zeros, and a preload output which represents the synchronized load chip select.

The pulse duration counter is preferably a 10 bit down counter. Microcontroller 2252 preferably controls the pulse duration such that a high-true 18 millisecond pulse (±100 microseconds) is obtained. The pulse duration counter is loaded by either the preload output or the RCO of the pulse duration counter. The RCO is in turn connected to a J–K flip flop, the output of which is the "vitrectomy" signal. This signal drives a solenoid drive 2290 which is in turn coupled to a vitrectomy valve 2254 in communication with pneumatic source 2201. The signal provides the user with cut rates preferably ranging between 30 cuts/minute (i.e., 2 seconds or 0.5 Hz) and 750 cuts/minute (i.e., 80 milliseconds or 12.5 Hz) and most preferably ranging between 30 cuts/minute (i.e., 2 seconds or 0.5 Hz) and 990 cuts/minute (60.61 ms or 16.5 Hz).

The cut rate of cutting blade 2224 of vitrectomy probe 2202 may be set by the user either via panel display 5 or foot control assembly 15, or remotely through a remote control (e.g., remote control 39). Vitrectomy module 2200 preferably supports at least three modes of operation, namely a linear cut mode, a fixed cut mode and a single cut mode. In the linear cut mode, the cut rate is controlled between a minimum cut rate and a maximum cut rate inputted by the user via panel 5, the remote control 39, or through right and left movements of the user's foot on the foot pedal. In the fixed cut mode, the cut rate is determined by the cut rate set by the user via panel 5 or remotely via the remote control 39, and right and left movements of the foot pedal of foot control assembly 15 are used to switch vitrectomy probe 2202 between an "on" and "off" position. The linear and fixed cut modes are preferably programmable so as to provide cut rates between approximately 30 cuts/minute to at least 750 and preferably 990 cuts/minute, in 1 cut/minute increments.

The single cut mode is provided with fixed, on/off control from panel 5. When the single cut mode is enabled, cutting blade 2224 of vitrectomy probe 2202 will close and open one time with a single activation.

The user can automatically adjust the pulse duration and cut rate of cutting blade 2224 on demand through any of the above-mentioned steps. In one embodiment of the invention, adjustments to the cut rate can be selected in increments of 30 cuts per minute. With such a configuration, vitrectomy control system 2250 can provide a user with a wide range of cut rates depending on the region of the eye in which vitrectomy probe 2202 is being used, the structure of the eye on which the user is operating and so forth.

Equipment parameters, such as the cut rate of cutting blade 224 of vitrectomy probe 2202, are preferably maintained in a non-volatile memory device, EEPROM or magnetic disk so that they may be preserved through power interruptions or intentional shutdown of microsurgical control system 1, and restored to their most recent settings upon power-up. Any user changes to these parameters will be immediately stored in the non-volatile memory device so that no special action is required by the user to initiate storage.

As previously mentioned, while the invention has been discussed in connection with the modular microsurgical control system shown in FIG. 1, the invention may also be implemented in a stand alone vitrectomy device 2280, the electrical components of which are shown in FIG. 6. The vitrectomy control system of vitrectomy device 2280 also centers around a single chip microcontroller 2282. In a preferred embodiment, microcontroller 2282 is a Motorola MC68HC11 microcontroller operating at 2 MHz. The memory and I/O address map for microcontroller 2282 is specified in the Motorola specification sheets for the MC68HC11 microcontroller, which are incorporated herein by reference. The vitrectomy device also includes various knobs, switches and displays for performing the various vitrectomy functions previously discussed herein and is controlled in a similar manner as that of vitrectomy module 2200 of FIG. 2.

Control of the cut rate for the vitrectomy probe of stand-alone vitrectomy device 2280 can be implemented in one of two ways. In one embodiment, a separate output compare bit of microcontroller 2252 is used. In another embodiment, real-time clock interrupts are used. The latter embodiment is preferably used when long pulse periods are desired. With such a configuration, vitrectomy control system 2250 provides the user with cut rates preferably ranging between 30 cuts/minute (i.e., 2 seconds or 0.5 Hz) and 750 cuts/minute (i.e., 80 milliseconds or 12.5 Hz) and most preferably ranging between 30 cuts/minute (i.e., 2 seconds or 0.5 Hz) and 990 cuts/minute (60.61 ms or 16.5 Hz).

Although the foregoing includes a description of the best mode contemplated for carrying out the invention, various modifications are contemplated.

As various modifications could be made in the constructions herein described and illustrated without departing from the scope of the invention, it is intended that all matter contained in the foregoing description or shown in the accompanying drawings shall be interpreted as illustrative matter rather than limiting.

What is claimed is:

1. A control system for surgical instruments, comprising:
   a pulse generator adapted to generate a plurality of pulses for driving a pulse-driven member of a surgical instrument, the plurality of pulses defining a pulse interval between each of the pulses, and each of the plurality of pulses having a pulse duration, the pulse interval and the pulse duration defining a pulse-driven member rate for the pulse-driven member of the surgical instrument; and
   a control mechanism coupled to the pulse generator for controlling the pulse duration and the pulse-driven member rate such that the pulse duration and pulse-driven member rate can be automatically changed over a range of pulse durations and pulse-driven member rates, respectively, on demand by an operator of the control system.

2. The control system of claim 1, wherein the control mechanism comprises a microcontroller having built in software controlled logic adapted to control the pulse duration and the pulse interval of the pulse generated by the pulse generator.

3. The control system of claim 2, wherein the software controlled logic of the microcontroller comprises a first timer for controlling the pulse duration of the pulse generated by the pulse generator, and a second timer for controlling the pulse interval of the plurality of the pulses generated by the pulse generator.

4. The control system of claim 2, wherein the software-controlled logic of the microcontroller comprises a timer adapted to control the pulse duration of each of the pulses generated by the pulse generator, and at least one clock interrupt adapted to control the pulse interval.

5. The control system of claim 1, wherein the pulse-driven member is a cutting blade and the pulse-driven member rate ranges between 30 cuts/minute and 990 cuts/minute.

6. The control system of claim 5 wherein the control mechanism comprises rate changing means for changing the pulse-driven member rate in increments of 30 cuts/minute.

7. The control system of claim 1, wherein the plurality of pulses generated by the pulse generator are pneumatically driven.

8. The control system of claim 1, wherein the plurality of pulses generated by the pulse generator are electrically driven.

9. The control system of claim 1, wherein the surgical instrument is a vitrectomy probe.

10. A microsurgical system, comprising:

a console;

a pulse generator adapted to generate a plurality of pulses for driving a pulse-driven member of a surgical instrument, the plurality of pulses defining a pulse interval between each of the pulses, and each of the plurality of pulses having a pulse duration, the pulse interval and the pulse duration defining a pulse-driven member rate for the pulse-driven member of the surgical instrument; and a control mechanism coupled to the pulse generator for controlling the pulse duration and the pulse-driven member rate such that the pulse duration and pulse-driven member rate can be automatically changed over a range of pulse durations and pulse-driven member rates, respectively, on demand by an operator of the control system.

11. The microsurgical system of claim 10, further comprising a plurality of ophthalmic modules removably coupled within the console of the microsurgical system, one of the ophthalmic modules comprising a surgical instrument port adapted to receive the surgical instrument.

* * * * *